(12) United States Patent
Thompson et al.

(10) Patent No.: US 10,682,268 B2
(45) Date of Patent: Jun. 16, 2020

(54) PROTECTIVE DISPOSABLE WRAPPER FOR TAMPONS

(71) Applicants: Carrie Thompson, Portland, OR (US); Scott Ketterer, Beaverton, OR (US)

(72) Inventors: Carrie Thompson, Portland, OR (US); Scott Ketterer, Beaverton, OR (US)

( * ) Notice: Subject to any disclaimer, the term of this patent is extended or adjusted under 35 U.S.C. 154(b) by 536 days.

(21) Appl. No.: 15/377,618

(22) Filed: Dec. 13, 2016

(65) Prior Publication Data

US 2017/0087032 A1    Mar. 30, 2017

Related U.S. Application Data

(63) Continuation of application No. 14/679,842, filed on Apr. 6, 2015, now Pat. No. 9,572,731, which is a continuation-in-part of application No. 14/214,059, filed on Mar. 14, 2014, now abandoned.

(60) Provisional application No. 61/799,357, filed on Mar. 15, 2013.

(51) Int. Cl.
    *A61F 13/34*    (2006.01)
    *A61F 13/551*   (2006.01)
    *A61F 13/20*    (2006.01)
    *A61F 13/26*    (2006.01)

(52) U.S. Cl.
    CPC ........ *A61F 13/5519* (2013.01); *A61F 13/202* (2013.01); *A61F 13/2074* (2013.01); *A61F 13/266* (2013.01); *A61F 13/34* (2013.01); *A61F 13/5518* (2013.01); *A61F 13/55175* (2013.01); *A61F 13/55185* (2013.01); *A61F 2013/55195* (2013.01)

(58) Field of Classification Search
    CPC ............ A61F 13/34; A61F 13/5515; A61F 13/55175; A61F 13/5518; A61F 13/55185; A61F 13/5519; A61F 2013/55195
    See application file for complete search history.

(56) References Cited

U.S. PATENT DOCUMENTS

| 3,035,578 A | 5/1962 | Elmore |
| 3,135,262 A | 6/1964 | Kobler |
| 3,674,029 A | 7/1972 | Bates et al. |

(Continued)

FOREIGN PATENT DOCUMENTS

| CN | 1306803   | 8/2001 |
| CN | 101204342 | 6/2008 |

(Continued)

OTHER PUBLICATIONS

Office action for U.S. Appl. No. 14/679,842, dated Jun. 17, 2016, Thompson et al., "Protective Disposable Wrapper for Tampons", 10 pages.

(Continued)

*Primary Examiner* — Catharine L Anderson
(74) *Attorney, Agent, or Firm* — Lee & Hayes, P.C.

(57) ABSTRACT

Tampon packaging and disposal systems and methods are disclosed. The packaging has a flexible mitten and an optional attached tampon enclosure. The tampon enclosure can package a tampon and the flexible mitten wraps around the tampon enclosure. When unwrapped, the tampon enclosure is detachable from the mitten and the tampon can be used by a user. The mitten is used for removing the used tampon worn by the user and disposing of the used tampon after removal.

20 Claims, 10 Drawing Sheets

(56) References Cited

U.S. PATENT DOCUMENTS

| | | | |
|---|---|---|---|
| 4,795,422 A | 1/1989 | Conner et al. | |
| 4,902,283 A | 2/1990 | Rojko et al. | |
| 5,000,315 A | 3/1991 | Butler | |
| 5,180,059 A | 1/1993 | Shimatani et al. | |
| 5,740,554 A | 4/1998 | Reed | |
| 5,827,251 A | 10/1998 | Moder et al. | |
| 5,827,256 A | 10/1998 | Balzar | |
| 5,911,712 A | 6/1999 | Leutwyler et al. | |
| 5,988,386 A | 11/1999 | Morrow | |
| 5,993,430 A | 11/1999 | Gossens et al. | |
| 6,299,607 B1 | 10/2001 | Osborn, III et al. | |
| 6,393,614 B1 | 5/2002 | Eichelbaum | |
| 6,402,727 B1 | 6/2002 | Rosengrant | |
| 6,516,469 B1 | 2/2003 | Schaetzel | |
| 6,687,911 B2 * | 2/2004 | Fitz | A41D 19/0075 2/163 |
| 6,939,333 B1 | 9/2005 | Franklin, Jr. | |
| 6,955,665 B2 | 10/2005 | Domeier et al. | |
| 6,994,696 B2 | 2/2006 | Suga | |
| 7,033,342 B2 | 4/2006 | Mizutani et al. | |
| 7,238,173 B1 | 7/2007 | Dobbs | |
| 7,601,146 B2 | 10/2009 | Mizutani et al. | |
| 7,727,209 B2 | 6/2010 | Mizutani et al. | |
| 8,012,137 B2 | 9/2011 | Lira | |
| 8,141,711 B2 | 3/2012 | Perry | |
| 8,317,765 B2 | 11/2012 | Loyd et al. | |
| 9,161,862 B2 | 10/2015 | Wolff | |
| 9,572,731 B2 * | 2/2017 | Thompson | A61F 13/5518 |
| 10,022,281 B1 * | 7/2018 | Ramsey | A61F 13/5518 |
| 2001/0049838 A1 | 12/2001 | Fitz | |
| 2004/0147892 A1 | 7/2004 | Mizutani et al. | |
| 2004/0147893 A1 | 7/2004 | Mizutani et al. | |
| 2004/0147894 A1 | 7/2004 | Mizutani et al. | |
| 2004/0147896 A1 | 7/2004 | Mizutani et al. | |
| 2004/0147898 A1 | 7/2004 | Mizutani et al. | |
| 2004/0162539 A1 | 8/2004 | Mizutani et al. | |
| 2004/0167491 A1 | 8/2004 | Mizutani | |
| 2004/0167492 A1 | 8/2004 | Mizutani et al. | |
| 2006/0004338 A1 | 1/2006 | Torkildsen et al. | |
| 2006/0212015 A1 | 9/2006 | Peele | |
| 2008/0027404 A1 | 1/2008 | Hernandez et al. | |
| 2008/0077104 A1 | 3/2008 | Baer et al. | |
| 2008/0077105 A1 | 3/2008 | Hooi | |
| 2008/0077107 A1 | 3/2008 | Minoguchi et al. | |
| 2008/0105579 A1 | 5/2008 | Arndt | |
| 2008/0154221 A1 | 6/2008 | Thornton | |
| 2009/0030394 A1 | 1/2009 | Mizutani et al. | |
| 2009/0204090 A1 | 8/2009 | Dennis et al. | |
| 2010/0076393 A1 | 3/2010 | Wasson et al. | |
| 2010/0152643 A1 | 6/2010 | Minoguchi et al. | |
| 2012/0053549 A1 * | 3/2012 | Knight | A61F 13/5515 604/385.13 |

FOREIGN PATENT DOCUMENTS

| | | |
|---|---|---|
| CN | 201399047 | 2/2010 |
| CN | 101677895 | 3/2010 |
| EP | 1079783 | 3/2001 |
| JP | 05-137751 A | 6/1993 |
| JP | 2010014603 A | 2/2010 |
| WO | WO2007096450 A1 | 8/2007 |
| WO | WO2014144811 | 9/2014 |

OTHER PUBLICATIONS

PCT Search Report and Written Opinion dated Jun. 25, 2015 for PCT Application No. PCT/US15/024564, 12 Pages.

PCT Search Report and Written Opinion dated Jul. 7, 2014 for PCT Application No. PCT/US14/029377, 9 Pages.

The Chinese Office Action dated Jan. 18, 2019 for Chinese Patent Application No. 201580024481.2, a counterpart of U.S. Pat. No. 9,572,731, 6 pages.

* cited by examiner

PROTECTIVE DISPOSABLE WRAPPER FOR TAMPONS

CROSS-REFERENCE TO RELATED APPLICATIONS

This application is a continuation of pending U.S. patent application Ser. No. 14/679,842, filed Apr. 6, 2015, which claims priority to U.S. patent application Ser. No. 14/214,059, filed Mar. 14, 2014, and to PCT/US2014/029377, also filed Mar. 14, 2014, the contents of which are herein incorporated by referenced in their entirety.

BACKGROUND

Many women worldwide use tampons during menstruation to help control or stop bleeding. The international medical community also uses tampons to help in medical applications like stopping or reducing bleeding from a bullet wound. Tampons are undeniably a part of modem culture and have grown to be a common household product with a large consumer base.

Because tampons absorb bodily fluids like blood and vaginal discharge, their use, removal, and disposal presents sanitary and other toxic exposure and disposal challenges. Tampons for personal use are oftentimes used and discarded in a private, unregulated setting, like a restroom at a business, which creates a situation that is ripe for exposure of the bodily fluids to people other than the tampon user and is also ripe for exposure of the bodily fluids to the tampon user herself.

Generally, tampons are currently available in a few forms—with and without a tube-in-tube style applicator. Regardless of the form, tampons are packaged in a disposable wrapper that, once opened, is no longer usable for any particular purpose and is promptly discarded. The current tampon wrappers provide a container for storing the tampon but serve no other purpose.

Frequently, the tampon user has to first remove the existing, used tampon before placing the new, fresh tampon. To do so, she uses her hand and usually extracts the tampon by gently pulling a string attached to the distal end of the tampon or pulls on the tampon itself. The tampon strings and the tampons can be difficult to grip especially if they are soaked in bodily fluids. Oftentimes during the extraction process, the tampon user comes into direct contact with her bodily fluids and also exposes her sensitive vaginal area to any contaminants that might be on her hands. Further, she discards the used tampon along with any other materials she might use to help remove the tampon, such as toilet paper or other paper products, in a nearby trash receptacle of some kind. For those tampons with applicators, the applicators are also discarded after being placed and they too are contaminated with bodily fluids.

The removal and disposal of tampons creates a sanitary and hygienic problem. The tampon users often have difficulty gripping the tampon or the tampon string to remove it. The tampon users and others are exposed to bodily fluids when they discard tampons in an uncontrolled environment like a restroom. During the extraction process, bodily fluids sometimes soil the tampon user's clothing or other items. The used tampons can create a foul odor and a toxic environment for those people who are tasked with cleaning the trash receptacles. Tampon packaging is not recycled or reused for any purpose and creates waste.

Therefore, there is a need in the art of tampon packaging to create a multi-purpose, sanitary, easy-to-use, cost-efficient packaging that has a low manufacturing cost.

SUMMARY

Aspects of the disclosure include tampon packaging and disposal systems that have a flexible mitten and a pocket along with a tampon enclosure. The flexible mitten has a continuous-tapered shape from a first end towards a second end. The first end of the flexible mitten defines an opening into a hollow interior space of the mitten. The second end of the mitten is sealed. The pocket extends away from an exterior surface of the mitten. The tampon enclosure is configured to store a tampon and is structured to be selectively detachable from the flexible mitten.

In other aspects of the disclosure, the tampon packaging and disposal systems include a flexible mitten and a pocket. The thickness of the material of the flexible mitten and the pocket can be 0.8 millimeters or less. The flexible mitten has a first end that defines an opening into a hollow interior space of the mitten. The flexible mitten also has a second end that is sealed. At least a portion of the flexible mitten has a tapered shape from the first end towards the second end of the mitten.

In still other aspects of the disclosure, methods of manufacturing a mitten for packaging and disposing tampons include providing a flexible mitten and a pocket on the flexible mitten. The flexible mitten has a continuously-tapered shape from a first end of the mitten towards a second end of the mitten. The first end of the mitten defines an opening into a hollow interior space of the mitten and the second end of the mitten is sealed. The pocket extends away from an exterior surface of the flexible mitten. The methods of manufacturing also include attaching a detachably attached tampon enclosure to the flexible mitten. The tampon enclosure is configured to store a tampon.

DETAILED DESCRIPTION

Tampon packaging and disposal systems and methods of using and manufacturing the disclosed systems offer a multi-purpose, cost-efficient tampon packaging that allows users to remove, contain, and discard used tampons and, optionally, a tampon applicator. The tampon packaging and disposal systems also store new tampons, in some examples. The packaging is lightweight and creates a more sanitary option for using and discarding tampons than conventional methods. The disclosed methods and systems provide a flexible mitten with a detachable tampon enclosure, the tampon can be stored in the enclosure and the user can remove the tampon stored in the enclosure and use the mitten for removal of and discarding the used tampon after use. The flexible mitten is thin and is rolled around the tampon enclosure so the combined package includes the tampon and the flexible mitten. The combined package of the tampon enclosure and the flexible mitten serves multiple purposes including helping the user to remove the used tampon and to provide a container for disposing of the used tampon and the applicator for the new tampon, if inserting a new tampon, all in a sanitary, efficient manner.

The material used to manufacture the flexible mitten is kept at a minimum and shaped in a way to prevent bunching of material around the user's fingertips during use and also keeps manufacturing costs low. The flexible mitten being rolled around the new tampon during storage also helps protect the new tampon from damage during storage. When the flexible mitten is rolled around the new tampon, it can be stored in the conventional exterior packaging for tampons that do not have a flexible mitten. The flexible mitten is versatile and easy to incorporate into current manufacturing techniques for tampon packaging.

I. The Tampon Packaging and Disposal System

Figure 1:
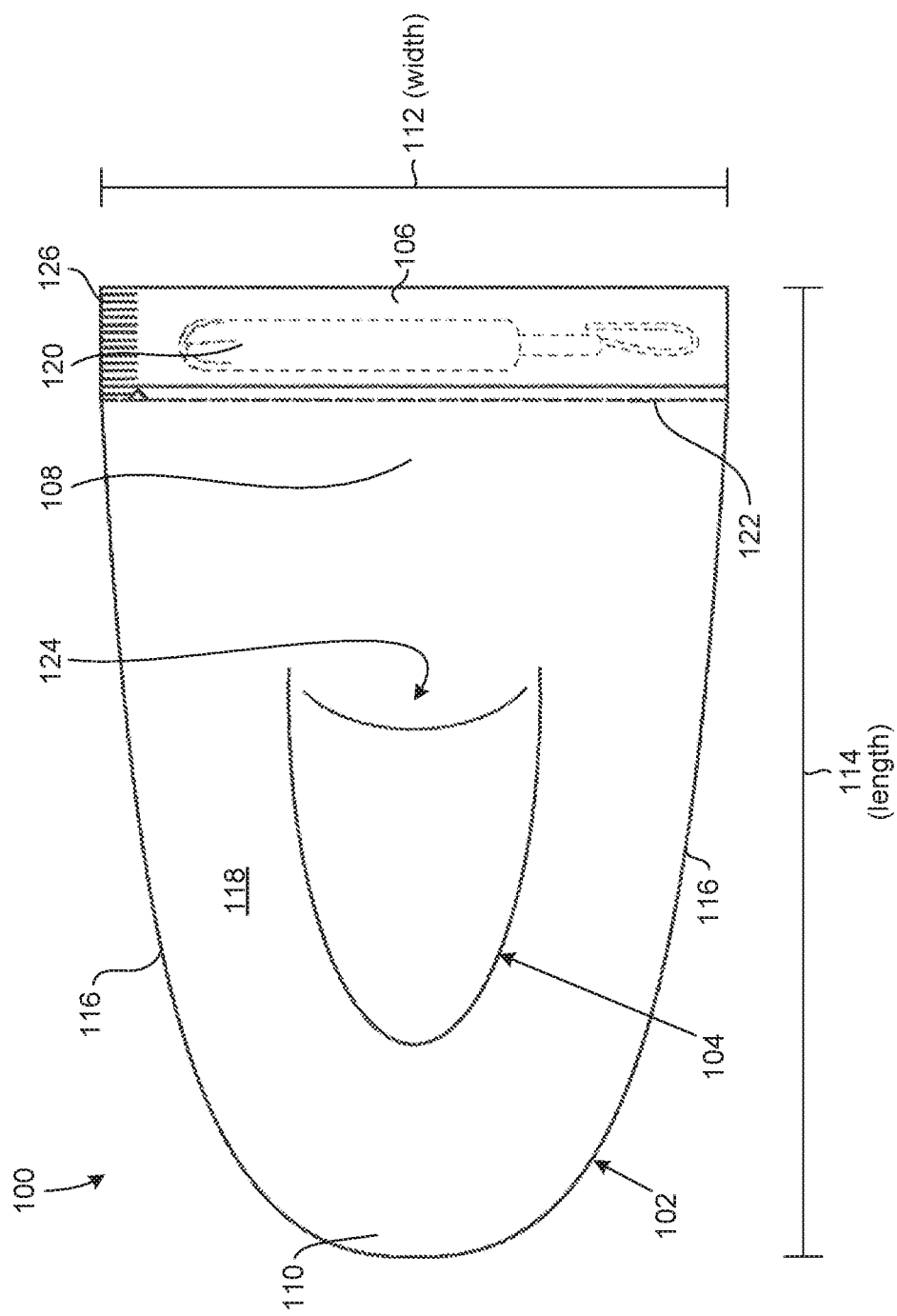
FIG. 1 is an example of a tampon packaging and disposal system, according to aspects of the disclosure.

FIG. 1 shows an example of a tampon packaging and disposal system 100 having a flexible mitten 102, a pocket 104, and a tampon enclosure 106. The flexible mitten 102 has a continuously-tapered shape, in this example, from a first end 108 of the mitten 102 towards a second end 110 of the mitten 102. The continuously-tapered shape means that the width 112 of the mitten 102 continuously becomes smaller along the length 114 of the mitten 102 from the first end 108 towards the second end 110.

In the example mitten 102 shown in FIG. 1, the continuously-tapered shape is curved although in other examples, a portion of the mitten may be curved and in still other examples some portions or all portions of the continuously-tapered mitten is linear. The first end 108 of the mitten 102 defines an opening into a hollow interior space of the mitten 102 and, much like an opening for any other mitten, allows a user to insert her hand into the mitten 102. The second end 110 of the mitten 102 and the side edges 114 along the length of the mitten 102 are sealed.

The tampon packaging and disposal system 100 has a pocket 104 that extends away from an exterior surface 118 of the mitten 102. The pocket 104 can accommodate a user's thumb when the user's hand is inserted into the mitten 102. When the user's hand is inserted into the mitten 102, the user is able to grip objects, such as tampons, between her fingertips positioned near the second, sealed end 110 of the mitten 102 and her thumb positioned in the pocket 104.

The tampon packaging and disposal system 100 shown in FIG. 1 has a tampon enclosure 106 that can store a tampon 120. The tampon enclosure 106 can be detachably detached from the rest of the mitten 102. The user, in this example, can detach the perforated edges 122 between the mitten 102 and the tampon enclosure 106. Any other suitable way to selectively detach the tampon enclosure from the mitten can be used. In alternative examples, the tampon enclosure is not attached to the mitten.

a. The Flexible Mitten

The flexible mitten 102 has a continuously-tapered shape, which means that the least amount material is needed at the sealed, second end 110 of the mitten 102. When a user inserts her hand into the mitten 102 and the user's fingertips are positioned at or near the second end 110 of the mitten 102, the mitten 102 accommodates the user's fingertips but the material does not bunch at the user's fingertips. The material is prevented from bunching at the user's fingertips during use because of the continuously-tapered shape of the mitten.

The continuously-tapered shape tracks the general outline of a user's hand when the user's hand is in an outstretched, flat position with fingers extended away from the user's wrist and the user's thumb tucked next to the palm of the user's hand. In this outstretched position, the flexible mitten is generally laying flat, although it is not tightly fitted around the user's hand (in the mitten) and thumb (in the pocket). Rather, the mitten and pocket fit somewhat loosely around the user's hand. The second, sealed end surrounds the user's fingertips with a curved shape to prevent excess material from gathering around the user's fingertips.

When a user has her hand inserted into the flexible mitten and moves her fingertips and thumb from the outstretched position together to grip an object, the flexible mitten contracts and, as a result, material gathers at her fingertips, among other places in the mitten. To keep the material gathering to a minimum, especially near the fingertips, the flexible mitten contracts along its continuously-tapered shape along the outline of the user's hand. While some material may still gather along the outline of the user's hand, as would happen anytime a mitten of any shape would contract, the continuously-tapered shape causes a more even gathering of material along the outline of the user's hand and prevents large bulk of material from gathering at any one or more points along the mitten than would non-tapered shape of any kind. For example, a square shaped mitten would cause a large gather of material at the distal corners of the mitten when the user contracted her hand, which would interfere with the user's ability to grip objects like a used tampon and/or a new tampon.

The continuously-tapered shape reduces, although may not eliminate, areas of bulky gatherings of material along the mitten when it contracts. The continuously-tapered shape can also produce a more uniform gathering of material along the outline of the user's hand rather than causing areas of bulky material gathering, such as the gathering of material in the square-shaped mitten discussed above. Specifically, the continuously-tapered shape of the mitten in the example system shown in FIG. 1 tracks the general outline and shape of a user's hand and consequently flexes with the user's hand rather than gathering in one or more places when the user contacts her hand.

For example, when the user contracts her hand within the mitten, the mitten material may slide along the outline of the user's hand, which is along the continuously-tapered, curved shape of the mitten shown in FIG. 1, and gather at various gathering places. Because of the continuously-tapered shape, especially at the areas of the second, sealed end that cover the user's fingertips, the material does not gather as bulk or excess material. The more uniform gathering of the mitten material when the mitten contracts and the reduction in bulky gatherings of material in any one or more places results in the user being able to grip objects easily, like a used or new tampon, without large quantities of bulky material interfering.

In some examples, such as the tampon packaging and disposal system 100 shown in FIG. 1, the entirety of the flexible mitten 100 is continuously-tapered from the first end 108, all the way to the second, sealed end 110. However, in some alternative examples, some portion, but not all, of the flexible mitten has a continuously-tapered shape. For instance, some example systems have a square, linear shape towards the first end and mid-portion of the flexible mitten and the second end that covers the user's fingertips has a continuously-tapered shape. The continuously-tapered shape differs from the non-continuously-tapered shape in its ability to prevent gathering of material, reduce the amount of material necessary for manufacturing, and help in the reversing out process of the mitten, as discussed further below.

As shown in FIG. 1, the first end 108 of the flexible mitten 102 has the largest diameter, and thus the most material, so it can accommodate the user inserting her hand into the mitten 100. Once the user's hand is inserted into the mitten 100, the opening at the first end 108 (not shown in FIG. 1) extends over the proximal end of the user's hand and, in some examples, over the user's wrist. The opening may have a cinching element that can secure the opening around the proximal end of the user's hand and/or the user's wrist, such as an elastic band, an adhesive strip, one or more ties, or hook and loop fasteners.

In other examples, such as the example shown in FIG. 1, the opening at the first end 108 of the mitten 102 has no cinching element. Rather, the opening freely gathers around the proximal end of the user's hand and/or the user's wrist when placed onto the user's hand, as discussed further below. The gathered material around the proximal end of the user's hand and/or the user's wrist does not interfere with the user's hand motion in gripping objects with the mitten between the user's fingertips and the user's thumb. Instead, the gathered material around the proximal end of the user's hand and/or the user's wrist can be used as an easy starting place to grip the second end of the mitten during the reversing out of the mitten after the used tampon has been removed and to contain the used tampon and optionally the used tampon applicator for the new tampon, if the user chooses to insert a new tampon, for disposal, which is discussed further below.

b. The Pocket

Referring again to FIG. 1, the tampon packaging and disposal system 100 shown has a pocket 104 that extends away from an exterior surface 118 of the flexible mitten 102. The pocket 104 is continuously-tapered in shape as it extends away from the exterior surface 118 of the mitten 102. Like the mitten, the pocket 104 is also curved in the example shown in FIG. 1 although it could be other shapes in alternative examples. An alternative could be a pocket with any portion being linear or curved with a beveled or otherwise angled edge. Any suitable shape can be used for the pocket.

When the user inserts her hand into the mitten 102, she positions her thumb within the pocket 104. Similar to the material gathering that is discussed above when the flexible mitten 102 contracts, the pocket 104 also contracts during use. In the example shown in FIG. 1, the pocket 104 is continuously-tapered in shape and is curved to surround an outline of the user's thumb. Here, the pocket's continuously-tapered, curved shape prevents the material of the pocket 104 from gathering bulk in any one or more places along the pocket 104.

Similar to the benefits of the continuously-tapered shape discussed above for the flexible mitten, the minimization of the material gathering improves the user's ability to grip objects with her thumb. When both the flexible mitten and the pocket are continuously-tapered and the gathering of material is minimized by the shape, the user is able to grip objects between her fingertips and thumb with little interference from the material gathering that inevitably happens when the user contracts her hand and the mitten with it.

The pocket 104 is positioned in a central portion 124 of the flexible mitten 102 in the example shown in FIG. 1. The pocket 124 is shown positioned about midway or more along the length 114 of the flexible mitten 102 and about midway across the width 112 of the flexible mitten 102. The positioning of the pocket along the height of the mitten may be selected based on a common user's hand, and more specifically, where a user's thumb might typically extend away from the user's hand. The opening between the flexible mitten and the pocket can be greater than the size of a typical user's thumb to accommodate multiple sizes and positions of users' thumbs.

As discussed above, the pocket 104 extends away from the flexible mitten 102 about midway across the width 112 of the flexible mitten 102 in the example shown in FIG. 1. The midway position of the pocket 104 accommodates ambidextrous use of the mitten 102 by both right- and left-handed users. The pocket can be positioned near one side or the other across the width of the flexible mitten to accommodate either a right- or a left-handed user, in alternative examples. However, the positioning of the pocket approximately midway across the width of the flexible mitten facilitates a right-handed user to insert her thumb into the pocket as easily as a left-handed user can insert her thumb into the pocket and thus the pocket is positioned for ambidextrous use.

c. The Tampon Enclosure

FIG. 1 also shows that the tampon packaging and disposal system 100 has a tampon enclosure 106. The tampon enclosure 106 is detachably attached to the flexible mitten 102 such that it can be removed from the mitten 102 by a user. The tampon enclosure 106 can store a new tampon 120, in some examples, and can have a removable edge 126 or tab in other examples that helps the user to open the tampon enclosure 106 and retrieve the new tampon 120. The tampon enclosure 106 shown in FIG. 1 is attached to the flexible mitten 102 by a perforated edge 122 that the user can tear to detach the tampon enclosure 106 from the flexible mitten 102. After the tampon enclosure 106 is separated from the flexible mitten 102, the user can then use the flexible mitten 102 to remove a used tampon (not shown in FIG. 1) and later use the new tampon 120 stored in the tampon enclosure 106 either after removal of the used tampon or at a later time of her choosing.

The tampon enclosure can be detachably attached to the flexible mitten in any suitable way including adhesives, hook and loop fasteners, and/or any other attachment element. In alternative examples, the tampon enclosure is not attached to the flexible mitten, but, rather, the flexible mitten is wrapped or rolled around the perimeter surface of the tampon enclosure when packaged and can be unrolled or unwrapped when the user wishes to use the flexible mitten and/or remove the new tampon from the tampon enclosure.

II. Examples of the Tampon Packaging and Disposal Methods

Figure 2A:
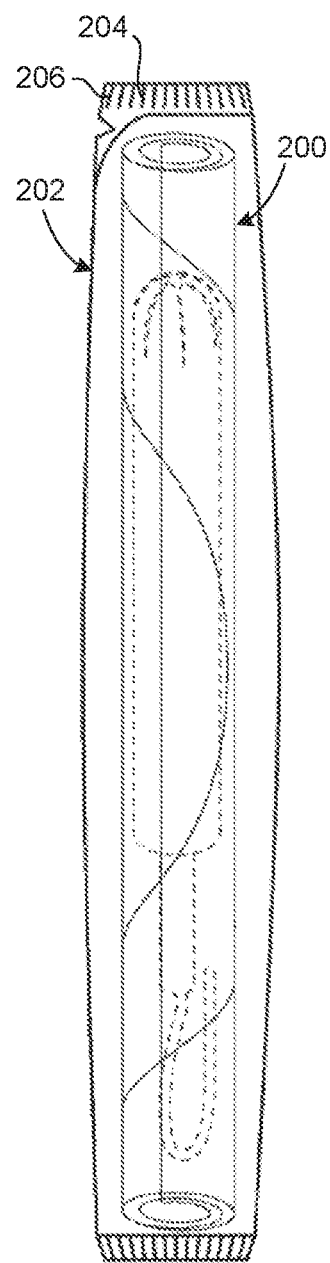
FIGS. 2A and 2B show an example of a rolled-up tampon packaging and disposal system sealed within and removed from an external packaging, respectively.
Figure 2B:
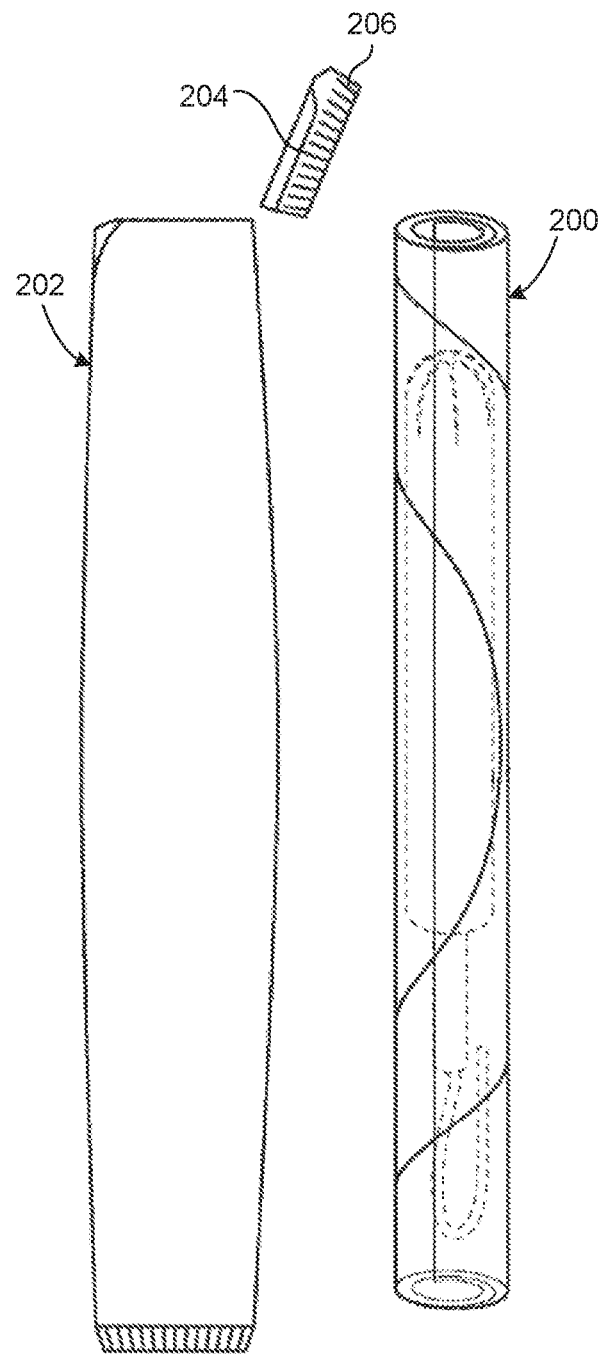

Turning now to FIGS. 2A and 2B, an example tampon packaging and disposal system 200 is shown positioned within an exterior packaging 202 and removed from the exterior packaging 202, respectively. FIG. 2A shows that the example tampon packaging and disposal system 200 is positioned within a sealed, exterior packaging 202 that can be helpful during storage, transport, and sales of the tampon packaging and disposal systems, among other benefits. The example tampon packaging and disposal system 200 is shown rolled with the flexible mitten wrapped around the tampon enclosure. FIG. 2B shows the rolled tampon packaging and disposal system 200 removed from the exterior packaging 202. The exterior packaging 202 shown in FIGS. 2A and 2B has an end 204 with a tab 206 that facilitates the removal of the end 204 from the remainder of the exterior packaging 202. The user removes the end 204 with by pulling on it near the tab 206.

The exterior packaging 202 shown in FIGS. 2A and 2B is a flexible material and can be the same exterior packaging that is conventionally used to package tampons. Because the flexible mitten is wrapped around the tampon enclosure and the flexible mitten is made of a thin, flexible material, its diameter is only slightly greater than the diameter of a tampon and therefore conventional tampon packaging can be used without manufacturing customized exterior packaging for the disclosed tampon packaging and disposal systems.

Figure 3:
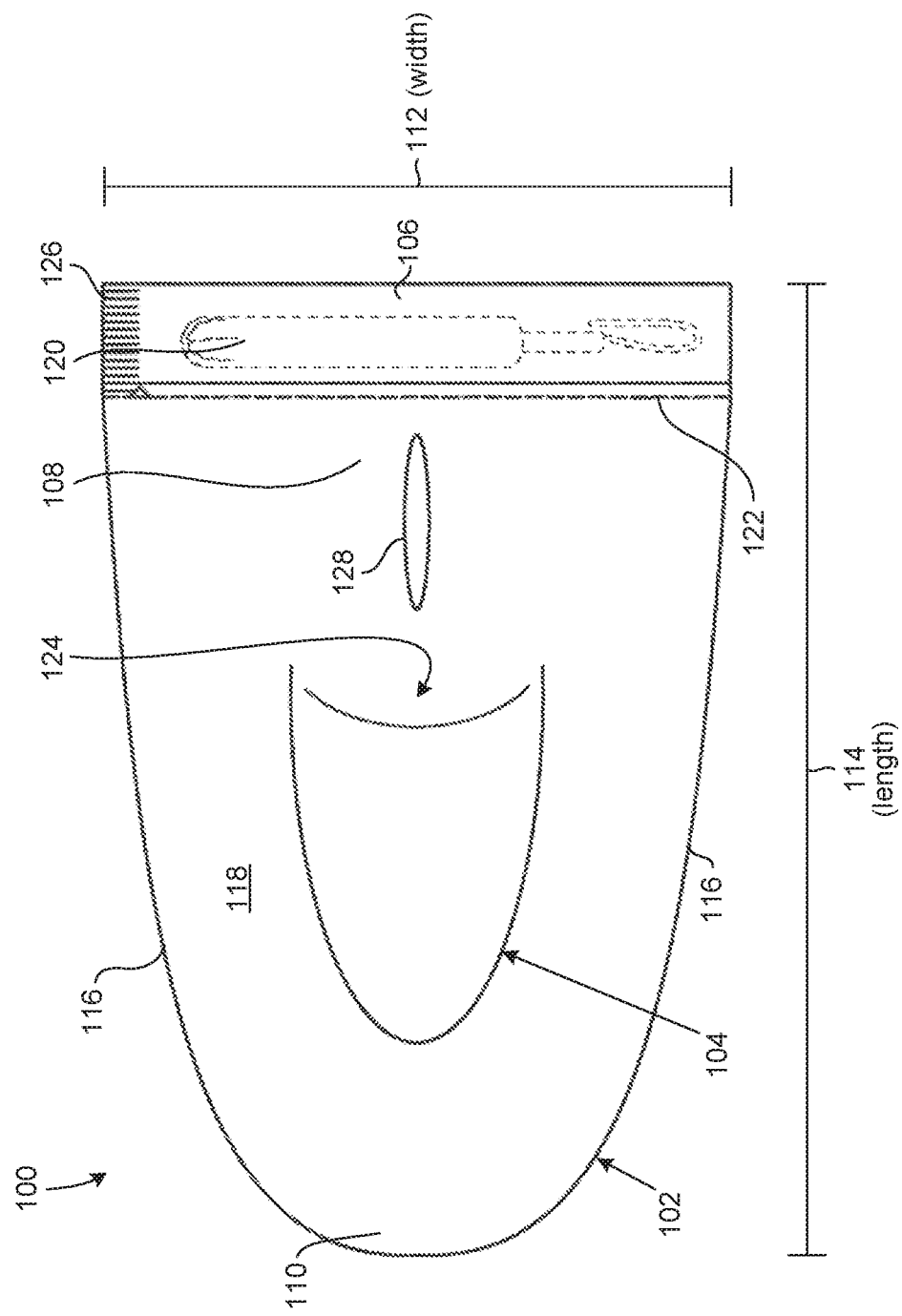
FIG. 3 is the example tampon packaging and disposal system from FIGS. 2A and 2B in an unrolled position without the external packaging.

FIG. 3 shows another example tampon packaging and disposal similar to the system shown in FIG. 1 with the addition of a set of slits 128 that can serve as a securing mechanism to contain a used tampon in the flexible mitten after it is reversed out so it can be discarded in a sanitary manner. The set of slits 128 extend transversely through the flexible mitten 102 from one exterior surface to the opposite exterior surface (not shown as separate surfaces in FIG. 3). The flexible mitten 102 has a hollow interior between two surfaces and the set of slits 128 create a slit in each of the two surfaces, approximately directly across from each other. While the set of slits are shown as being the same shape in the example shown in FIG. 3, the slits can be different shapes from each other and/or can be shapes other than slits.

Because the flexible mitten 102 has a hollow interior, the set of slits 128 extend through both surfaces of the flexible mitten 102. When the user's hand is inserted into the mitten 102, the two surfaces of the flexible mitten extend away from each other to accommodate the user's hand and the set of slits 128 are positioned approximately over the proximal end of the user's hand and/or the user's wrist directly across from each other on opposing sides. The set of slits 128 are shaped to accommodate the second end of the twisted, reversed out mitten when the used tampon is threaded through the set of slits 128 to secure the system closed, as described further below.

Figure 4:
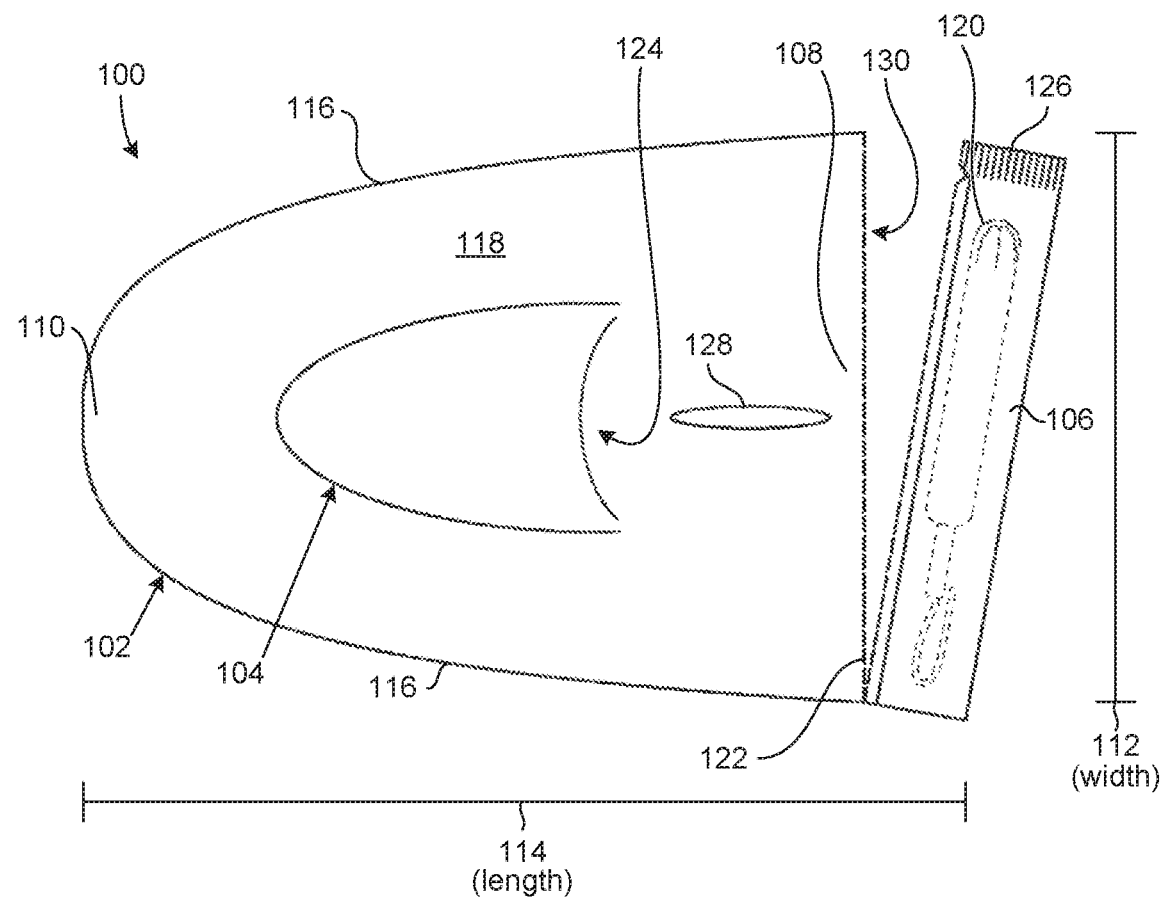
FIG. 4 shows the unrolled example tampon packaging and disposal system from FIG. 3 with the tampon enclosure partially detached.

FIG. 4 shows the tampon packaging and disposal system 100 shown in FIG. 3 with the tampon enclosure 106 mostly detached from the flexible mitten 102. Detaching the tampon enclosure 106 exposes the opening 130 of the flexible mitten 102. As discussed above, the opening 130 is located at the first end 108 of the flexible mitten 102 and the user can insert her hand through the opening 130 to position the flexible mitten 102 over her hand for use.

Figure 5:
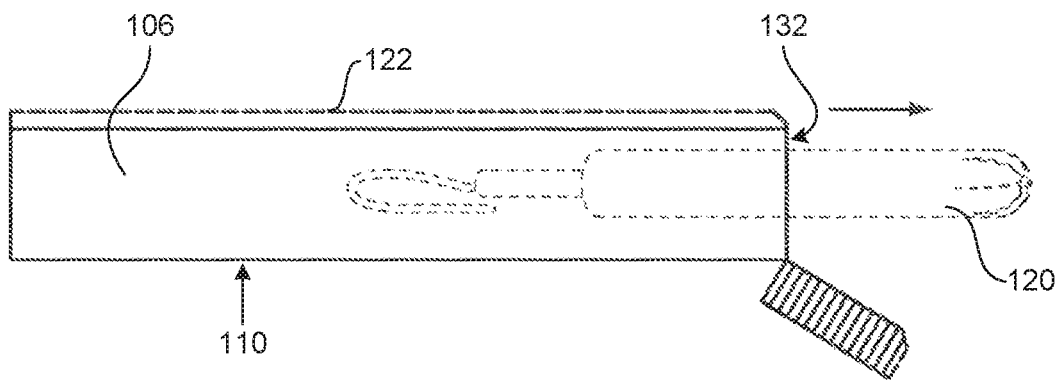
FIG. 5 shows an example tampon partially removed from the tampon enclosure of the example tampon packaging and disposal system shown in FIGS. 3 and 4.

FIG. 5 shows the tampon enclosure 106 after it was detached from the flexible mitten 102 along its perforated edge 122. The tampon enclosure 106 is generally a sealed package for the tampon 120. The tampon enclosure 106 can be opened so the user can remove the tampon 120. In the example show in FIG. 5, one end 126 of the tampon enclosure 106 is removed to provide access to the interior 132 of the tampon enclosure 106 and allow the new tampon 120 to be removed.

Figure 6:
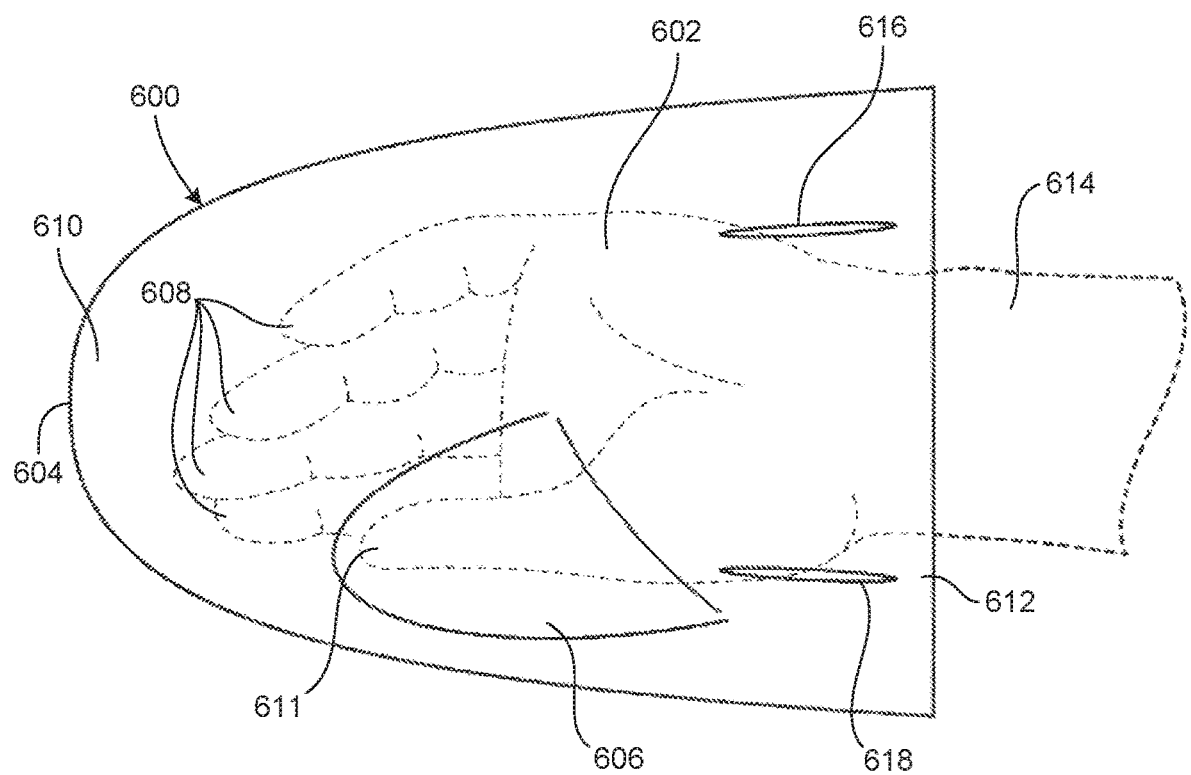
FIG. 6 shows another example flexible mitten with the tampon enclosure removed and a user's hand inserted.

FIG. 6 shows another example tampon packaging and disposal system 600 with a user's hand 602 inserted within it. Similar to the example systems described above, this example system 600 has a flexible mitten 604 and a pocket 606. The user's fingers 608 extend into the sealed, second end 610 of the flexible mitten 604 while the user's thumb 611 extends into the pocket 606 of the mitten 604. The first end 612 of the mitten 604 extends around the user's wrist 614, in this example, and can extend any length up the user's arm in other examples.

The example tampon packaging and disposal system 600 shown in FIG. 6 has an enclosure element that includes two sets of slits 616, 618. Similar to the single set of slits enclosure element described above, either one or both of the two sets of slits 616, 618 can receive the second end of the twisted, reversed out mitten that contains the used tampon. Either the twisted, reversed out mitten can be threaded back through one set of slits 616, the other set of slits 618, or both sets of slits 616, 618 to contain the used tampon and optionally the applicator for the new tampon after it is inserted and the tampon enclosure or other items to be discarded.

Figure 7B:
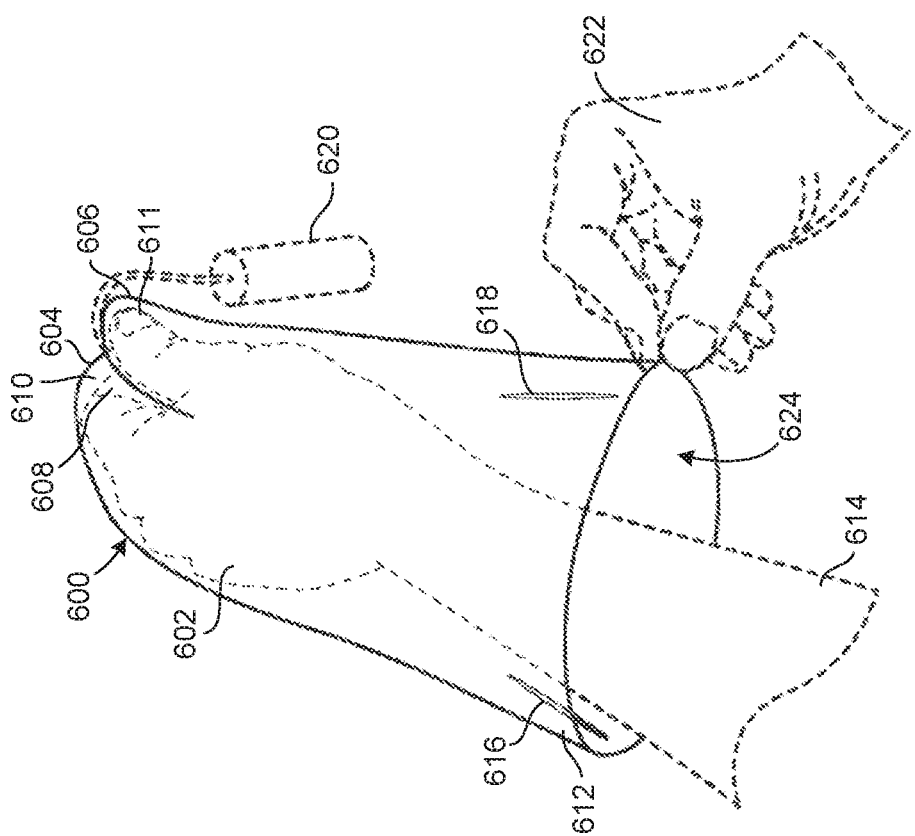
FIG. 7B shows a user beginning a reversing-out process to contain the used tampon in the reversed-out flexible mitten.
Figure 7A:
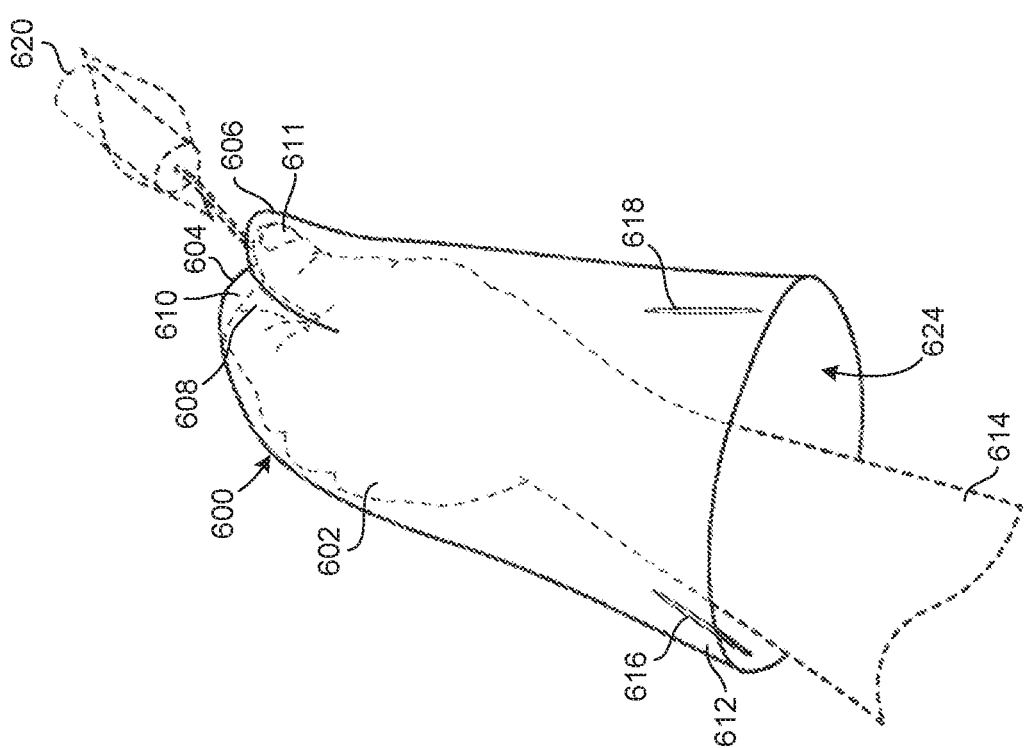
FIG. 7A shows a user using the flexible mitten to remove a used tampon.
Figure 8:
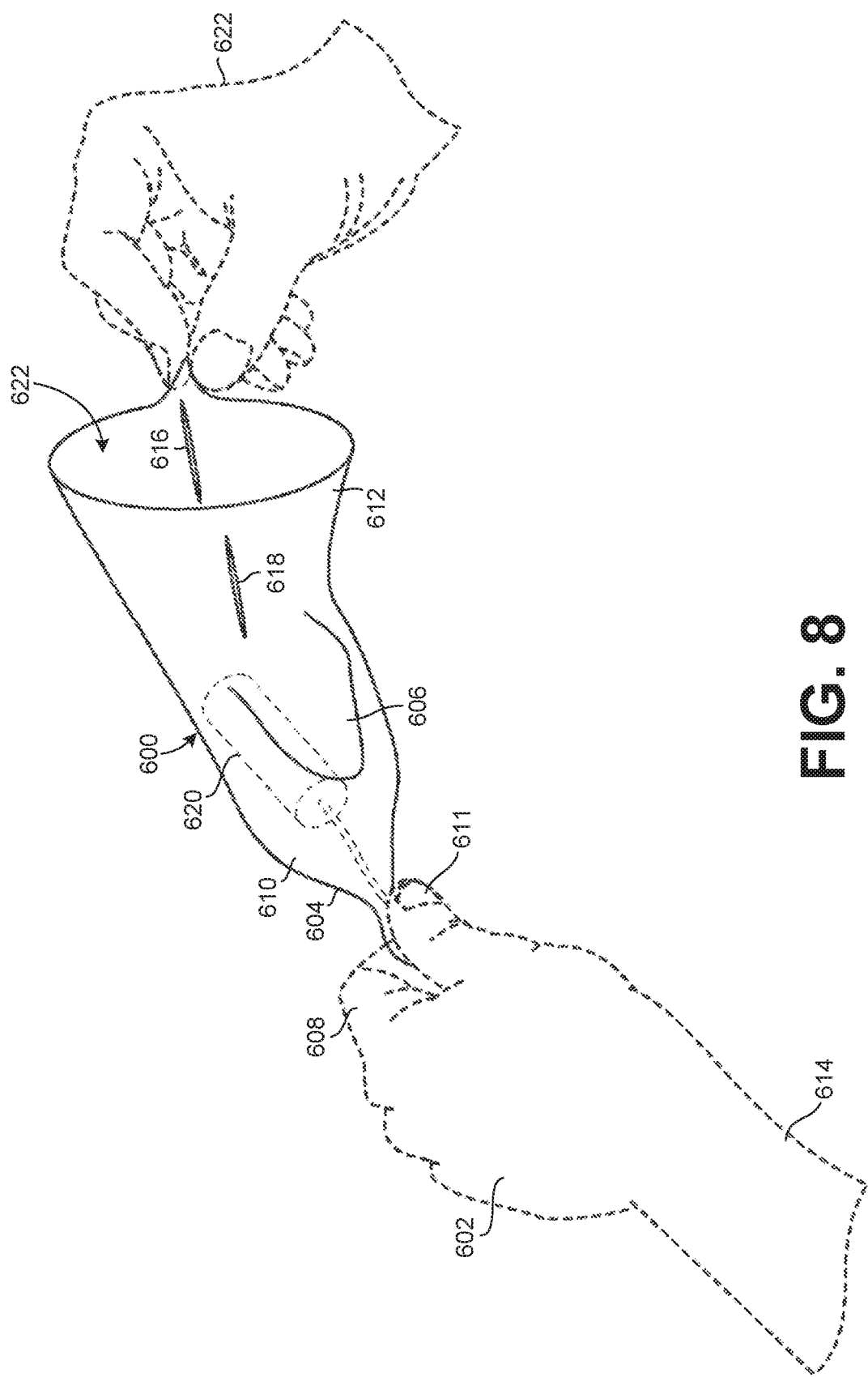
FIG. 8 shows a user completing the reversing-out process to contain the used tampon in the reversed-out flexible mitten.

FIGS. 7A-8 show the process of reversing out the example tampon packaging and disposal system 600 shown in FIG. 6. FIG. 7A shows a user removing a used tampon 620 with the mitten 604 by gripping a string of the tampon between her fingers 608 and thumb 611. FIG. 7B shows the used tampon 620 removed and the user gripping the used tampon 620 between her fingers 608 and thumb 611 with her hand covered by the mitten 604. With her opposite hand 622, the user grips the first end 612 of the mitten 604 near or close to the first end of the mitten at or near the opening 624 to begin reversing out the mitten 604. Reversing out the mitten 604 means to turn the mitten 604 inside out. When the user grips the used tampon 620 and reverses out the mitten 604, the used tampon 620 is then contained within the reversed out mitten 604 without the user ever touching it directly with her hand at any time throughout the removal process.

The reversing out process is facilitated by the continuously-tapered shape of the mitten. As the user draws the first end back over the mitten towards the second end in the reversing out process, the width of the mitten becomes continuously smaller because of the continuously-tapered shape. The continuously smaller width of the mitten as the first end is reversed out back over mitten towards the second end continuously causes the width of the drawn end—the first end and subsequently the middle portion of the mitten—to be greater than the width of the mitten being drawn through the first end.

Because the width of the drawn end is always greater than the width of the end being drawn through the first end, the mitten easily glides over itself during the reversing out process. The continuously-tapered shape always causes a portion of the mitten being drawn over another portion of the mitten during the reversing out process to have a greater diameter being drawn over a smaller diameter. At no point during the reversing out process is the user required to draw a portion of the mitten with a smaller diameter over a portion of the mitten with a larger diameter—the reversing out process is continually going from larger diameter towards smaller diameter because of the continuously-tapered shape.

FIG. 8 shows the reversed out mitten 604 containing the used tampon 620 and being held between the user's two hands 602, 622. The user may set aside the reversed out mitten 604 containing the used tampon 620 and insert the new tampon (not shown in FIG. 8). After the user inserts the new tampon, the tube-in-tube style applicator or any other type of applicator and tampon enclosure material needs to be discarded. Oftentimes the applicator(s) are exposed to bodily fluids during the new tampon insertion process and would benefit from a sanitary disposal system as well. The reversed out mitten 600 shown in FIG. 8 has room to contain any used applicators and tampon enclosure material in addition to the used tampon. If the user chooses to place a used applicator and/or the tampon enclosure into the reversed out mitten 604, the combination of the used tampon, the used applicator, and the tampon enclosure is contained in the reversed out mitten 604 and can be discarded in a sanitary manner. With the disclosed systems, the user has the ability to place any object, whether it contacts bodily fluid or not, into the reversed out mitten for sanitary disposal.

Figure 9A:
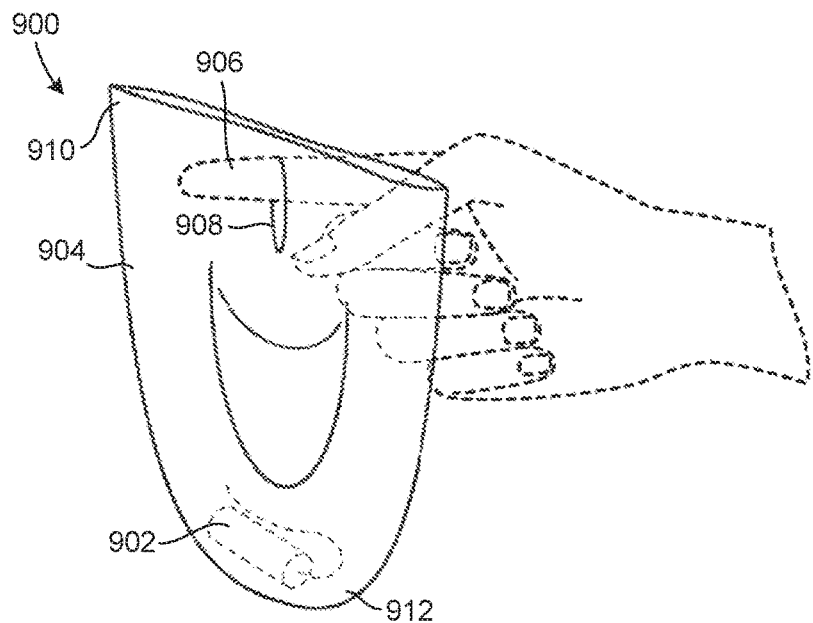
FIG. 9A shows a user holding the flexible mitten with the used tampon contained in it.

FIGS. 9A-10B show an example tampon packaging and disposal system 900 that secures the used tampon 902 in a reversed out mitten 904 for disposal. The reversed out mitten 904 shown in FIGS. 9A-10B is similar to the example mitten shown in FIG. 3 and discussed above. FIG. 9A shows the used tampon 902 contained in the second end of the reversed out mitten 904. The user has inserted her finger 906 through the set of slits 908, which gives the first end 910 of the mitten 904 a secure base around which to twist the remainder of the mitten. The set of slits 908 provides the user with a place to insert her finger 906 to perform the twisting of the mitten 904, but the user can alternatively twist the remainder of the mitten in any suitable manner without inserting her finger. For example, the user could hold the first end of the mitten and twist without inserting her finger through the set of slits.

Figure 9B:
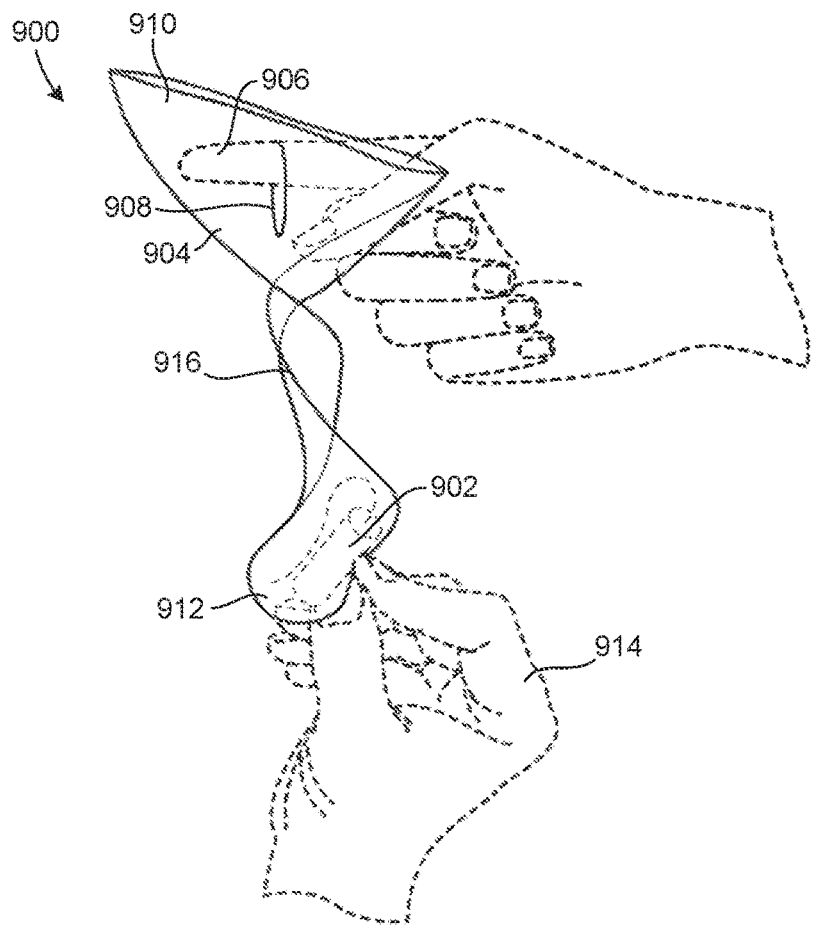
FIG. 9B shows a user twisting the flexible mitten containing the used tampon.
Figure 10A:
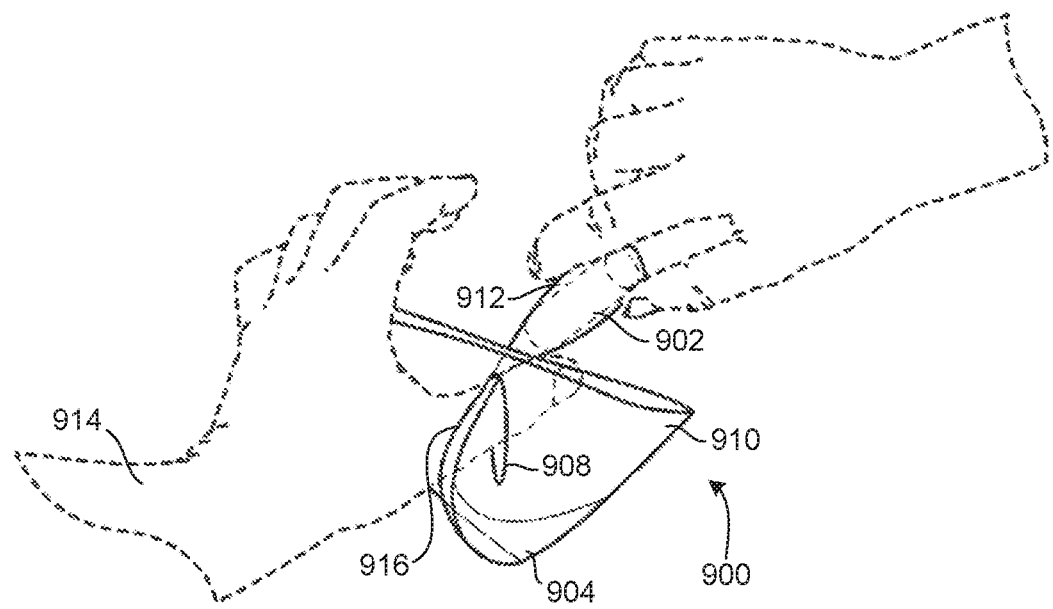
FIG. 10A shows a user threading the portion of the twisted flexible mitten containing the used tampon through slits in the flexible mitten.

FIG. 9B shows the user taking her opposite hand 910 and twisting the mitten by gripping the second, sealed end 912 of the mitten 904 and twisting against the stationary first end 910 of the mitten 904. The central portion 916 of the mitten 904 becomes twisted as a result with the used tampon 902 being contained at the second, sealed end 912 of the mitten 904. The user can then thread the second, sealed end 912 of the mitten 904 through the set of slits 908, as shown in FIG. 10A. While the user is shown to be twisting the reversed out mitten in FIG. 9B, the user is not required to twist the mitten before threading through the slits.

The set of slits 908 shown in the example mitten shown in FIGS. 9A-10B is longer than it is wide. The mitten 904 includes a flexible material and the width of the set of slits 908 can flex to expand to accommodate the second end 912 of the mitten 904 being threaded through it. Once the second end 912 of the mitten 904 is threaded through the set of slits 908, the width of the set of slits 908 contracts back to its original width and the tampon 902 contained in the second end 912 of the mitten 904 can be positioned so its length extends across the width of the set of slits so the second end 912 remains threaded through the set of slits 908. Even if the threaded tampon were to move from the position of its length extending across the width of the slits, the width of the tampon is greater than the width of the slits so the tampon would still hold itself in the threaded position through the slits.

Figure 10B:
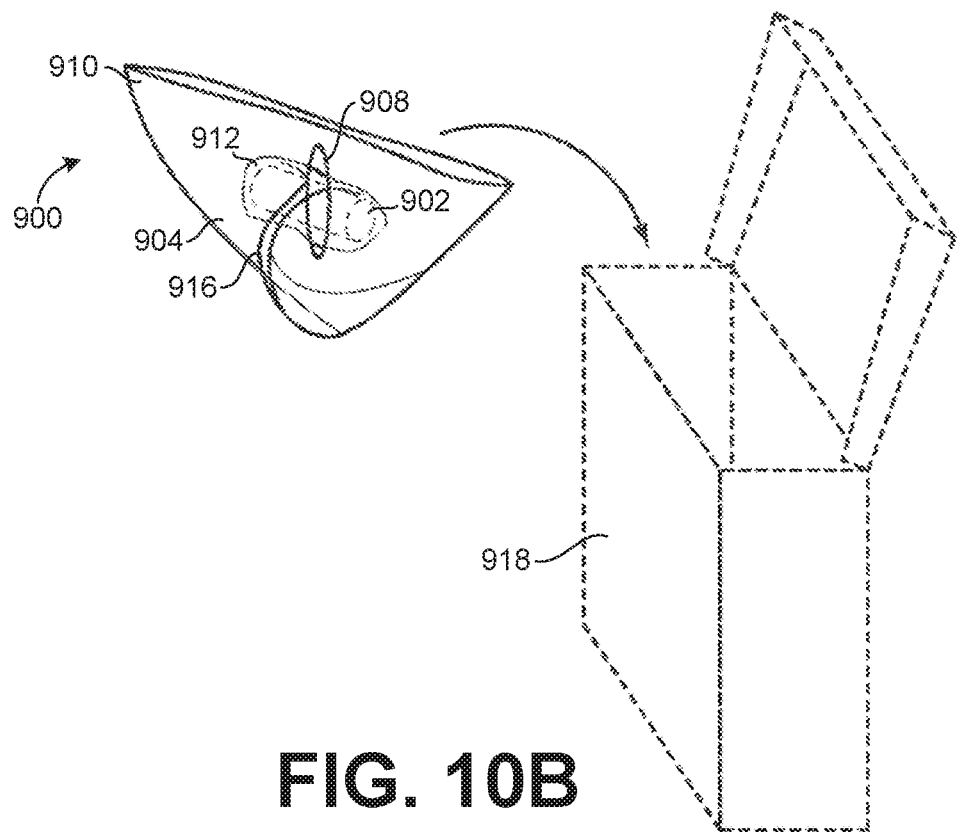
FIG. 10B shows the threaded used tampon contained in the flexible mitten and being disposed in a receptacle.

For example, the second end 912 of the mitten 904 is threaded through the set of slits 908 in FIG. 10B. The used tampon 902 is contained within the second end 912 of the mitten 904 and it is positioned so its length extends across the width of the set of slits 908. The used tampon 902 in the threaded second end 912 of the mitten 904 holds the second end 912 securely threaded through the set of slits 908 in a manner similar to how a button is threaded through a buttonhole. FIG. 10B also shows how the used tampon 902 contained in the threaded mitten 904 can be discarded in a receptacle 918 of any kind. The used tampon 902 is wholly contained in the mitten 904 and can be discarded in a sanitary manner in the receptacle 918.

Figure 11:
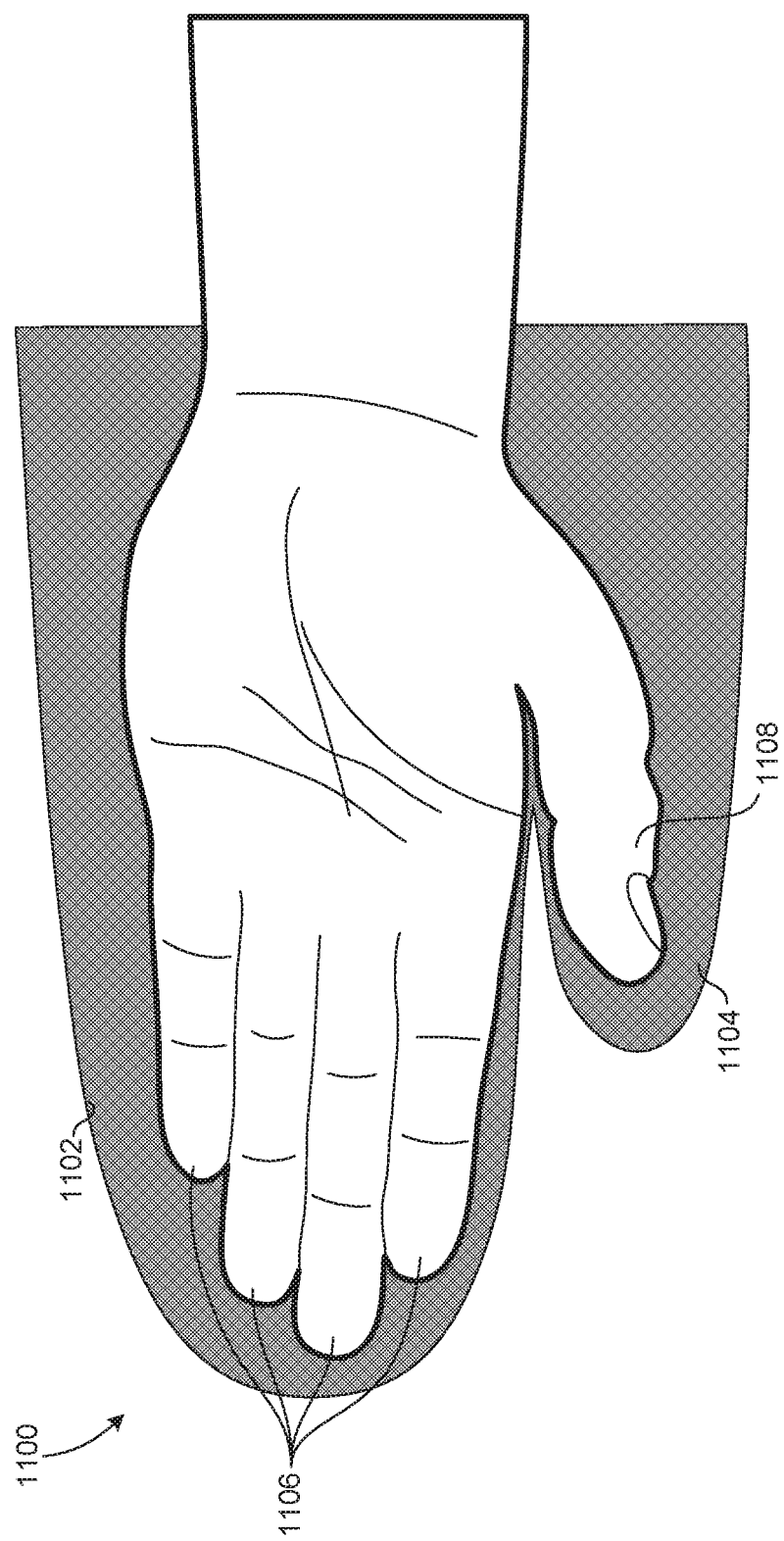
FIG. 11 shows yet another example tampon packaging and disposal system.

FIG. 11 shows an alternative embodiment of a tampon packaging and disposal system 1100. The system 1100 has a flexible mitten 1102 and an integral pocket 1104. Instead of extending away from the exterior surface of the flexible mitten like the example pockets discussed above, the integral pocket 1104 is formed as a part of the flexible mitten 1102 and can be considered an extension of the flexible mitten 1102 where the user's fingers are inserted. The opening at the first end of the flexible mitten opens directly into both the portion of the mitten 1102 into which the user's fingers 1106 are inserted and the pocket 1104 into which the user's thumb 1108 is inserted.

III. Methods of Manufacturing Tampon Packaging and Disposal Systems

Any of the above example tampon packaging and disposal systems can be manufactured using conventional manufacturing techniques and without a significant increase in either materials or cost to manufacture as compared to the conventionally made tampon packaging. The continuously-tapered shape of the mitten provides an efficient manner in which to manufacture the mitten by keeping the material to a minimum while still providing the sanitary protection over the user's hand in a functional way and reducing the likelihood that the material gathers into a bulk when the user is contracting and flexing the mitten during use. The amount of material needed to manufacture the mitten is kept at a minimum because the continuously-tapered shape of the mitten extends along the outline of the user's hand rather than in a square or other alternative shape that has excess material that is not a functional part of the tampon packaging and disposal system.

For example, two sheets of flexible material are placed over each other and one end and the edges are sealed in the continuously-tapered shape, as shown in the examples in FIGS. 1 and 3. The other end remains open and forms the opening into which the user can insert her hand. The opening becomes the first end of the mitten and the sealed end becomes the second end of the mitten. The pocket can be added to the mitten by forming a hole on one side of the exterior surface of the mitten and attaching the opening of the pocket to the hole on the exterior surface. The pocket can be added either before or after the two sheets of flexible material are sealed together.

Once the mitten is formed, the tampon enclosure can optionally be attached to the first end of the mitten, which seals the opening in a closed position at the first end. The seam between the first end of the mitten and the tampon enclosure is sealed and a perforated edge, a notch, or other mechanism for easily separating the tampon enclosure from the mitten can be created after it is attached to the mitten. Still further, a set of slits or multiple sets of slits can be optionally stamped or cut through the first and second sheets of flexible material on the mitten to form the slit-style securing elements discussed above.

The tampon packaging and disposal systems are then optionally packaged in an exterior packaging for distribution, storage, and/or protection. The exterior packaging is oftentimes flexible although it can be any suitable material. Because the mitten is flexible, it can be rolled or wrapped around the perimeter surface of the tampon enclosure in a relatively fitted, tight arrangement so that the flexible mitten is not creating excess bulk around the perimeter of the tampon enclosure. Once the mitten is tightly rolled against the perimeter surface of the tampon enclosure, the diameter profile of the tampon packaging and disposal system is only slightly greater than the diameter of a tampon enclosure by itself For example, the thickness of the mitten is 0.8 millimeters (mm) or less and would likely be rolled around the tampon enclosure two or three times, which increases the diameter of the tampon packaging and disposal system approximately 1.6 mm to 2.4 mm. The increased diameter of approximately 1.6 mm to 2.4 mm in this example can fit within the conventional exterior packaging for a tampon.

During the manufacturing process, the sheets that form the mitten are sealed together either by a heat or light sealing process(es), adhesive(s), bond(s), fusing, or any other manner in which to seal the sheets together. Further, the manner in which the tampon enclosure is attached to the mitten can be any suitable manner including having two sheets sealed to form both the mitten and the tampon enclosure in the same sealing process. In this example, the pocket is added and the perforated edge formed at the seal between the mitten and the tampon enclosure is stamped after it has been sealed. As discussed above, the sealing of the mitten in the continuously-tapered shape allows for the excess material to be reused or otherwise recycled, which keeps materials to a minimum and keeps manufacturing costs low.

IV. Materials and Other Features of the Tampon Packaging and Disposal Systems

Any of the above example tampon packaging and disposal systems can include one or more flexible materials, such as any suitable polymer(s). For example, the sheets that form the flexible mitten can be a thin polymer, such as polyethylene, non-polyethylene, and/or polylactic acid based plastics. The thickness of the sheets used to form the mitten can be 0.8 mm, in some examples, or less, which, in flexible polymer material(s) facilitates the sheets of the mitten to be rolled or wrapped around an object, like the tampon contained in the tampon enclosure in the above-discussed example systems. Other thicknesses for the sheets of material(s) forming the mitten can also be used and the thickness of the sheets may or may not be uniform throughout the sheet. For example, the thickness of the sheet could be greater where the first end of the mitten is to be formed to provide the user with some additional thickness with which to grip the mitten during the reversing out process.

The material(s) used to form the mitten are fluid impermeable in some examples, meaning that they are capable of containing fluids, such as bodily fluids, and objects, like a used tampon and/or the applicator for the new tampon, if the user chooses to insert a new tampon at that time. The fluid impermeable material(s) prevent fluid exchange across the material to the exterior of the mitten when the used tampon(s) and/or used applicator(s) are contained within the reversed out mitten. The material(s) provide a barrier for the fluid to escape and thus prevent exposure to the bodily fluids contained in the mitten. Alternatively, the material(s) selected for the mitten can be semi-fluid-impermeable rather than fluid impermeable.

The material(s) used to form the disclosed tampon packaging and disposal systems can also be biodegradable. The selected material(s) may also have some elastic properties to endure contact with objects during storage and transport. Still further, one or more surfaces or a portion of the surfaces of the mitten can be lined with a deodorizing or scent-neutralizing coating or liner that helps to reduce or eliminate scents produced by any contents contained in the mitten or from its surroundings. An anti-septic coating can be added to any of the surfaces of the mitten as well.

The dimensions of the mitten can be approximately six (6) inches wide by approximately nine (9) inches long with the pocket being approximately one (1) inch wide by six (6) inches long, in some examples. Other mittens vary in any of these dimensions. The mittens may also be formed in multiple sizes associated with common groups of different sized users, such as small, medium, and large sizes that correlate to users with generally small, medium, and large sized hands compared to the general population.

The disclosed tampon packaging and disposal systems can be packaged together with multiple systems included in a single kit or they can be packaged separately. Any suitable type of tampon can be included in the tampon enclosure. The color of the mitten can be any suitable color and/or transparency. In some examples, the mitten is a dark, opaque color that helps to discretely discard of the used tampon and/or applicator.

The features disclosed in the foregoing description, or the following claims, or the accompanying drawings, expressed in their specific forms or in terms of a means for performing the disclosed function, or a method or process for attaining the disclosed result, as appropriate, may, separately, or in any combination of such features, be used for realizing the invention in diverse forms thereof.

The invention claimed is:

1. A tampon disposal system, comprising:
   a mitten having;
      two flexible sheets that are sealed along a perimeter of the mitten to define a first hollow interior space that is configured to receive fingers;
      a pocket centered approximately at a mid-way position across a width of the mitten between opposite side portions of the perimeter, wherein the pocket defines a second hollow interior space that is configured to receive a thumb, and wherein the pocket is sized to fit loosely over the thumb; and
      an opening along at least an end portion of the perimeter at an end of the mitten, wherein the opening opens directly into both the first hollow interior space and the second hollow interior space.

2. The tampon disposal system of claim 1, wherein the mitten has a continuously-tapered shape.

3. The tampon disposal system of claim 1, wherein the mitten is a square or rectangular shape.

4. The tampon disposal system of claim 1, wherein the opening of the mitten is sized to accommodate multiple sizes of hands of a user.

5. The tampon disposal system of claim 1, wherein the mitten has a deodorizing coating.

6. The tampon disposal system of claim 1, wherein the end portion of the perimeter along which the opening is defined includes a perforated edge.

7. The tampon disposal system of claim 6, further comprising:
a tampon enclosure attached to the mitten by the perforated edge that runs along the end portion of the perimeter at the end of the mitten, the tampon enclosure storing an unused tampon and including a removable edge or tab for opening the tampon enclosure to retrieve the unused tampon from the tampon enclosure,
wherein the perforated edge is configured to be torn to detach the tampon enclosure from the mitten, thereby exposing the opening of the mitten to receive a hand of a user.

8. The tampon disposal system of claim 1, wherein the two flexible sheets are sealed by one or more of a heat or light sealing process, adhesive, bonding, or fusing.

9. The tampon disposal system of claim 1, wherein the mitten is structured to be reversed out back over a hand of a user to obtain a reversed out mitten, and the reversed out mitten is structured to contain one or more of a used tampon, an applicator of a new tampon, or a packaging of the new tampon.

10. The tampon disposal system of claim 1, further comprising a securing element attached to the flexible mitten and structured to selectively seal the opening of the mitten.

11. The tampon disposal system of claim 10, wherein the securing element is structured to seal the opening of the mitten after the mitten has been reversed out back over a hand of a user.

12. The tampon disposal system of claim 10, wherein the securing element includes at least one set of slits that extends through the mitten from one exterior surface of the mitten to an opposite exterior surface of the mitten.

13. The tampon disposal system of claim 10, wherein the securing element includes at least two sets of slits that extend through the mitten from one exterior surface of the mitten to an opposite exterior surface of the mitten.

14. The tampon disposal system of claim 10, wherein the securing element includes at least one of a drawstring, tabs, one or more handles, or an adhesive element.

15. The tampon disposal system of claim 1, wherein the mitten includes at least one of polyethylene or polylactic acid.

16. The tampon disposal system of claim 1, wherein the mitten includes a material that has at least one of biodegradable or anti-septic characteristics.

17. The tampon disposal system of claim 1, wherein a thickness of a material of the mitten is 0.8 millimeters or less.

18. A tampon disposal system, comprising:
a mitten having:
a first end;
a second end opposite the first end;
a first side;
a second side opposite the first side, wherein the second end of the mitten, the first side of the mitten, and the second side of the mitten are sealed to define a first hollow interior space that is configured to receive fingers;
a pocket centered approximately at a mid-way position across a width of the mitten between the first side and the second side, wherein the pocket defines a second hollow interior space that is configured to receive a thumb; and
an opening at the first end of the mitten that opens directly into both the first hollow interior space and the second hollow interior space.

19. The tampon disposal system of claim 18, further comprising:
a tampon enclosure attached to the mitten at the first end of the mitten by a perforated edge that runs along the width of the mitten, the tampon enclosure storing an unused tampon and including a removable edge or tab for opening the tampon enclosure to retrieve the unused tampon from the tampon enclosure,
wherein the perforated edge is configured to be torn to detach the tampon enclosure from the mitten, thereby exposing the opening of the mitten to receive a hand of a user.

20. The tampon disposal system of claim 18, wherein the mitten further includes a set of slits that extends through the mitten from one exterior surface of the mitten to an opposite exterior surface of the mitten, the set of slits being usable as a securing mechanism to contain a used tampon in the mitten after the mitten has been turned inside out.

* * * * *